United States Patent [19]
Bell et al.

[11] Patent Number: 5,779,687
[45] Date of Patent: Jul. 14, 1998

[54] METHOD OF REMOVING UNDESIRABLE FLUID FROM RESPIRATION PASSAGES BY SUCTION CATHETER ASSEMBLIES

[75] Inventors: Craig J. Bell, Winchester; William Hollister, E. Sullivan, both of N.H.

[73] Assignee: Smiths Industries Public Limited Company, London, England

[21] Appl. No.: 601,347

[22] Filed: Feb. 16, 1996

Related U.S. Application Data

[63] Continuation of Ser. No. 301,438, Sep. 8, 1994, abandoned, which is a continuation of Ser. No. 949,978, Sep. 24, 1992, abandoned.

[51] Int. Cl.⁶ ............................................. A61M 5/32
[52] U.S. Cl. .................. 604/265; 128/207.16; 604/28; 604/119; 604/35
[58] Field of Search ........................ 604/265, 266, 604/27, 28, 29, 52, 53, 119, 171, 163, 184, 101, 103, 43, 45, 280, 283, 35; 128/DIG. 21, 207.14, 207.16; 427/2.1, 2.12, 2.24, 2.25, 2.27, 2.28, 2.3

[56] References Cited

U.S. PATENT DOCUMENTS

| | | |
|---|---|---|
| 3,598,127 | 8/1971 | Wepsic . |
| 3,991,762 | 11/1976 | Radford ........................ 604/119 |
| 4,054,139 | 10/1977 | Crossley ....................... 604/265 |
| 4,510,933 | 4/1985 | Wendt et al. ................ 128/207.14 |
| 4,581,028 | 4/1986 | Fox, Jr. et al. . |
| 4,623,329 | 11/1986 | Drobish et al. ................ 604/29 |
| 4,772,275 | 9/1988 | Erlich .......................... 604/280 |
| 4,925,668 | 5/1990 | Khan et al. .................... 424/422 |
| 5,013,306 | 5/1991 | Solomon et al. . |
| 5,073,164 | 12/1991 | Hollister et al. ............... 604/43 |
| 5,083,561 | 1/1992 | Russo . |
| 5,139,018 | 8/1992 | Brodsky et al. .............. 128/207.14 |
| 5,181,908 | 1/1993 | Bell ............................. 604/24 |
| 5,277,177 | 1/1994 | Page et al. .................. 128/200.26 |
| 5,325,851 | 7/1994 | Reynolds et al. ............. 128/207.16 |
| 5,340,359 | 8/1994 | Segura Badia ................ 604/283 |
| 5,354,267 | 10/1994 | Niermann et al. ............. 604/32 |
| 5,451,215 | 9/1995 | Wolter ......................... 604/265 |
| 5,460,613 | 10/1995 | Ulrich et al. ................. 604/118 |
| 5,490,503 | 2/1996 | Hollister ...................... 128/205.12 |
| 5,520,664 | 5/1996 | Bricault, Jr. et al. .......... 604/265 |

FOREIGN PATENT DOCUMENTS

| | | |
|---|---|---|
| 2056660 | 9/1992 | Canada ....................... 604/280 |
| 229862 | 7/1987 | European Pat. Off. . |
| 328421 | 8/1989 | European Pat. Off. . |
| 379269 | 7/1990 | European Pat. Off. . |
| 3302567 | 1/1983 | Germany . |
| 3435553 | 9/1984 | Germany . |
| 86/02561 | 5/1986 | WIPO . |
| 9001956 | 3/1990 | WIPO . |

*Primary Examiner*—Michael Buiz
*Assistant Examiner*—At Nguyen
*Attorney, Agent, or Firm*—Pollock, Vande Sande & Priddy

[57] ABSTRACT

A method of removing undesirable fluid from the respiration passages of a patient uses a closed system suction catheter assembly having a protective sleeve enclosing an aspirating catheter extending through a sliding seal in a patient coupling. The catheter has an antimicrobial surface such as formed by silver sulfadiazine which reduces the accumulation of bacteria while the catheter is within the protective sleeve and prolongs the useful life of the assembly.

8 Claims, 1 Drawing Sheet

METHOD OF REMOVING UNDESIRABLE FLUID FROM RESPIRATION PASSAGES BY SUCTION CATHETER ASSEMBLIES

This application is a Continuation of U.S. patent application Ser. No. 08/301,438, filed Sep. 8, 1994, abandoned which is a Continuation of U.S. patent application Ser. No. 7/949,978, filed Sep. 4, 1992, now abandoned.

BACKGROUND OF THE INVENTION

This invention relates to suction catheter assemblies.

The invention is more particularly concerned with assemblies of the kind having an aspirating catheter enclosed within a protective, flexible sleeve and which can be advanced through a coupling at one end of the assembly. The coupling has one port connected to a tracheal tube and two further side ports by which ventilation of the patient can take place. In use, the machine end of the catheter is connected to a suction source via a valve. Secretions that build up on the inside of the tracheal tube, the trachea and bronchi can be periodically removed by advancing the catheter through the coupling and down the tracheal tube and opening the valve. The coupling enables ventilation of the patient to continue while suctioning takes place.

Examples of catheter assemblies having an aspirating catheter which is contained within a sleeve and which can be pushed through a sliding seal on a coupling are described in several patents, such as U.S. Pat. No. 3,991,752 to Radford; U.S. Pat. No. 4,569,344 to Palmer; U.S. Pat. No. 4,638,539 to Palmer; U.S. Pat. No. 4,696,296 to Palmer; U.S. Pat. No. 4,825,859 to Lambert; U.S. Pat. No. 4,834,726to Lambert; U.S. Pat. No. 4,836,199 to Palmer; U.S. Pat. No. 4,838,255 to Lambert; U.S. Pat. No. 4,872,579 to Palmer; U.S. Pat. No. 4,938,741 to Lambert; U.S. Pat. No. 4,967,743 to Lambert; U.S. Pat. No. 4,981,466 to Lambert; U.S. Pat. No. 5,025,806 to Palmer; U.S. Pat. No. 5,029,580 to Radford; U.S. Pat. No. 5,060,646 to Page; U.S. Pat. No. 5,065,754to Jensen; U.S. Pat. No. 5,073,164 to Hollister; and GB 2207736 to Hollister. Suction catheter assemblies of this kind are also available from Smiths Industries Medical Systems Inc under the trade mark STERICATH and from Ballard Medical Products Inc under the trade mark TRACHCARE.

The sliding seal in the assembly removes some of the secretions clinging to the outside of the aspirating catheter each time it is withdrawn but, nevertheless, some will remain on the external surface of the catheter. These secretions contain microbes from the patient that can colonize to larger populations and present a potential risk to the patient on reintroduction of the catheter. In some assemblies, irrigating fluid can be applied to the outside of the catheter which helps remove secretions but does not completely remove them.

The environment within the protective sleeve encourages the multiplication of bacteria on the outside of the catheter and, for this reason, the time for which the suction catheter assembly can be used is generally limited to about 24 hours. This is a disadvantage because each time the assembly has to be removed and replaced, ventilation of the patient must be interrupted. The opening of the ventilation circuit can allow external microbes to be introduced into the patient causing nosocomial infections. Also, the repeated replacement of the assemblies leads to increased cost and waste, with the consequent disposal difficulties involved with soiled surgical products. Closed system suction catheter assemblies have considerable advantages to the user compared with conventional suction catheters so it is highly desirable for the cost of using the assemblies to be kept as low as possible in order to encourage their use. Any assembly which can be used safely for a longer period would, therefore, bring with it cost savings and advantages to the patient.

SUMMARY OF THE INVENTION

It is an object of the present invention to provide a suction catheter assembly which can be used for a longer period.

According to one aspect of the present invention there is provided a suction catheter assembly for use in removing undesirable fluid from a patient, the catheter assembly comprising: an aspirating catheter having a proximal end and a distal end, said distal end being suitable for insertion into a patient; a vacuum connecting member located in the vicinity of the proximal end of the aspirating catheter; a patient connecting member mounted to surround the aspirating catheter in the vicinity of the distal end of the aspirating catheter, the patient connecting member having a sliding seal with the outside of the aspirating catheter; a protective sleeve extending along the aspirating catheter where it extends between the patient connecting member and the vacuum connecting member, the aspirating catheter having at least an external surface with antimicrobial properties such that the accumulation of bacteria on the external surface of the catheter is reduced when the catheter is withdrawn into the protective sleeve.

The antimicrobial surface is preferably provided by an antimicrobial substance in the bulk material of the catheter. Alternatively, an antimicrobial coating could be formed on the surface of the catheter. The antimicrobial surface may be provided by a substance including a silver compound such as silver sulfadiazine. The antimicrobial substance may include a silver compound with a binder such as aluminosilicate or hydroxyapitate. Alternatively, the antimicrobial substance may include a silver compound with a polymer attachment substace. The antimicrobial substance may include chlorhexidene. The aspirating catheter may be substantially of PVC.

According to another aspect of the present invention there is provided a suction catheter assembly for use in removing undesirable fluid from a patient, the catheter assembly comprising: an aspirating catheter having a proximal end and a distal end, said distal end being suitable for insertion into a patient; a vacuum connecting member located in the vicinity of the proximal end of the aspirating catheter; a patient connecting member mounted to surround the aspirating catheter in the vicinity of the distal end of the aspirating catheter, the patient connecting member having a sliding seal with the outside of the aspirating catheter; a protective sleeve extending along the aspirating catheter where it extends between the patient connecting member and the vacuum connecting member, the assembly having an antimicrobial substance on a component thereof effective to reduce transfer of bacteria from the external surface of the catheter to the patient.

It has previously been proposed to coat catheters which remain in the body for prolonged periods with an antimicrobial substance so as to reduce the risk of infection. Examples of these previous catheters include urinary catheters and venous catheters (such as the Arrow Antiseptic Multi-Lumen Central Venous Catheter). These catheters remain in the body and are disposed of after use. By contrast, in the present invention the catheter remains outside the body for the majority of the time and is periodically inserted and removed through a sliding seal. It has been discovered that an antimicrobial surface on an aspirating catheter is effective to reduce the build up of bacteria outside the body and that the antimicrobial properties remain effective even though the catheter passes repeatably through a sliding seal.

A suction catheter assembly according to the present invention, will now be described, by way of example, with reference to the accompanying drawings.

Description of the Preferred Embodiments

Figure 1:
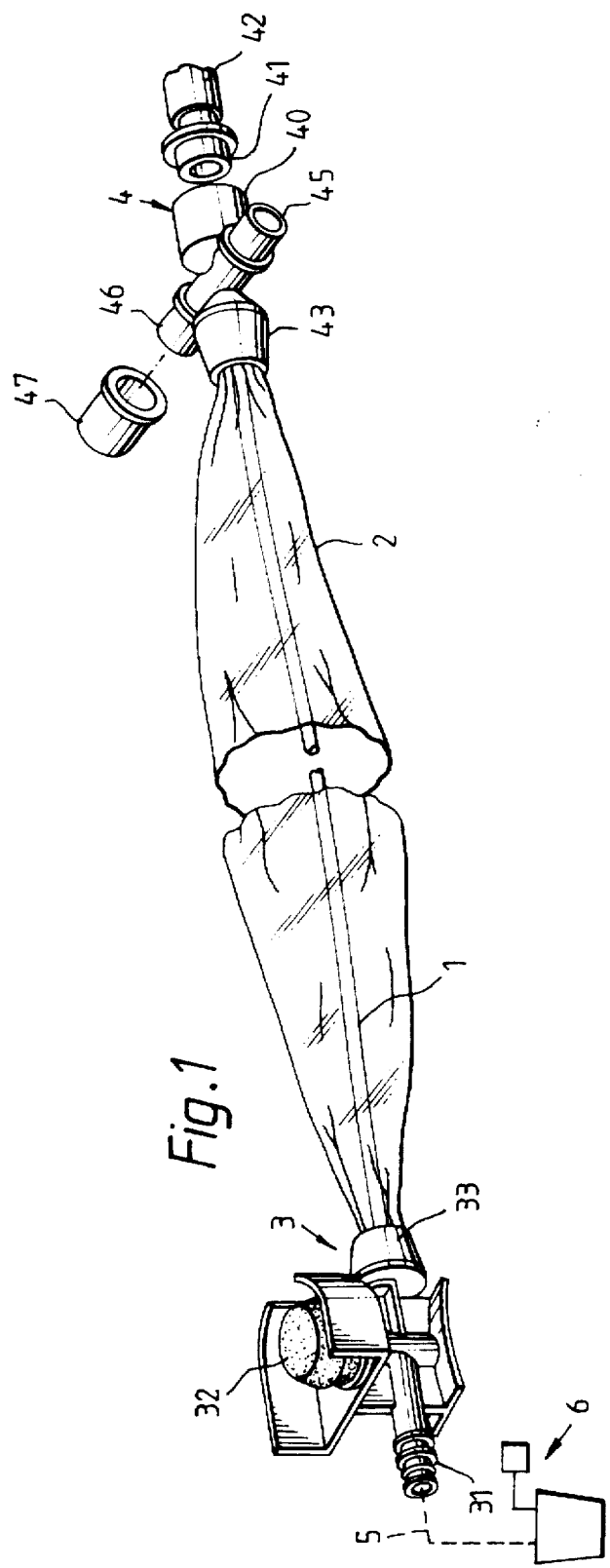
FIG. 1 is a perspective view of the assembly; according to the invention.
Figure 2:
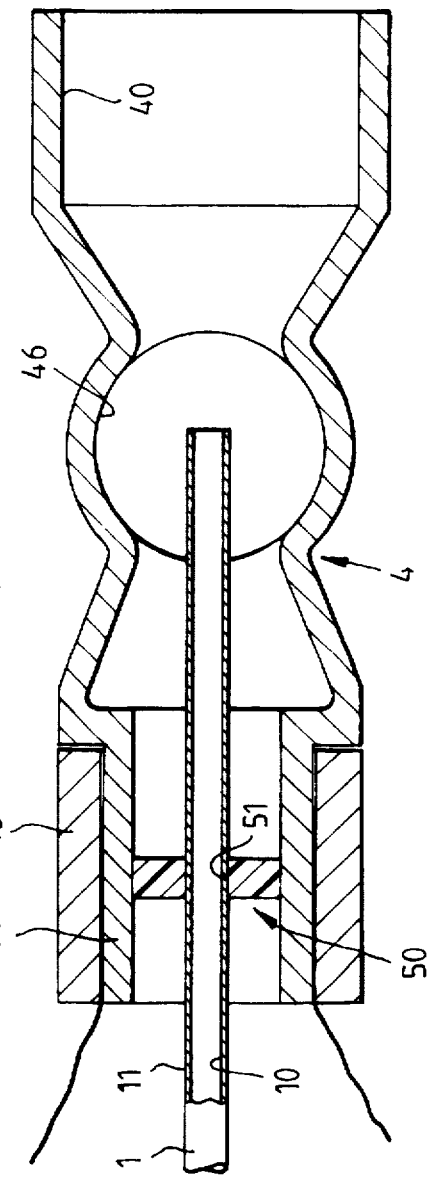
FIG. 2 is a sectional view of the assembly; in a larger scale.

The suction catheter assembly comprises an aspirating catheter 1 that extends within a flexible, protective sleeve 2 between a vacuum connecting member 3 and a patient connecting member 4.

The aspirating catheter 1 has an outside diameter of about 4–5 mm and a length of about 55 cm. In the illustrated example, the catheter 1 has a single lumen 10 although catheters with multiple lumens for use in irrigation, oxygen supply or medication delivery could be used. At its machine or proximal end, the catheter 1 is secured to the vacuum connecting member 3.

The vacuum connecting member 3 is molded from a rigid plastics material and has a bore (not shown) extending along it into one end of which the catheter 1 is bonded. The opposite end of the bore extends through a spigot 31 which, in use, is connected to tubing 5 which extends to a vacuum or suction source 6. The vacuum connecting member 3 includes a conventional manually-operated valve 32 which normally prevents flow through the connecting member 3 and catheter 1 but which can be pressed down by the user to open the valve and connect the lumen 10 of the catheter to the suction source 6.

The proximal end of the sleeve 2 is secured to the vacuum connecting member 3 beneath a threaded collar 33 secured to the distal end of the vacuum connecting member. The distal end of the sleeve 2 is similarly secured to the patient connecting member 4 by means of a threaded collar 43 which is screwed onto a threaded, proximal extension 44 of the patient connecting member.

The patient connecting member 4 is of generally cruciform shape. At its distal, or patient end, the connecting member 4 has a female luer coupling 40 which is aligned with the axis of the member and with the proximal extension 44. The coupling 40 is adapted to be connected to a cooperating coupling 41 on the end of a tracheal tube 42. Two side ports 45 and 46 extend at right angles to the axis of the connecting member, directly opposite one another, about midway along the length of the connecting member. These two side ports 45 and 46 communicate directly with the interior of the coupling 40 and are used in the conventional manner to connect with ventilation apparatus. One port may be used for inhalation gas and the other port used for exhalation gas. Alternatively, one of the ports 46 may be closed by a cap 47 and inhalation and exhalation both be effected through the other port 45.

The patient connecting member 4 includes a sliding seal 50 in the form of a resilient diaphragm with a central aperture 51 through which extends the aspirating catheter as a close sliding fit.

The aspirating catheter 1 is mainly of PVC but contains an antimicrobial substance so that it has an external surface 11 which has antimicrobial properties. The antimicrobial substance is blended with polymer pellets, in a proportion of about 3–10% by weight substance to polymer, prior to extrusion of the catheter so that the wall of the catheter is antimicrobial throughout its thickness and has antimicrobial properties on both its internal and external surfaces. Alternatively, the external antimicrobial surface may be formed by coating or otherwise forming an antimicrobial layer on the external surface only.

The antimicrobial substance may be silver sulfadiazine or chlorhexidine. Alternatively, a silver ion with a binder such as alumino-silicate, hydroxyapatite or a polymer attachment substance such as polyurethane could be used. Combinations of these materials, such as, silver sulfadizine and chlorhexidine could also be used.

In operation, the coupling 40 of the connecting member 4 is secured to a coupling 41 on the end of a tracheal tube 42 and its side ports 45 and 46 are connected to a ventilator. The vacuum coupling member 3 is connected to the suction source 6 but, as long as the manual valve 32 remains unactuated, no suction is applied to the catheter 1.

When aspiration of fluid from the trachea or bronchi is required, the user grips the catheter 1 through the sleeve 2 and pushes it forwardly so that the distal, patient end of the catheter is advanced through the connecting member 4 and into the tracheal tube 42. When the catheter 1 has been inserted to the desired depth, the user depresses the valve 32 so that the catheter is connected to the suction source 6 and fluid in the vicinity of the tip of the catheter is sucked into the catheter and removed. During aspiration, ventilation of the patient occurs normally. When aspiration is complete, the catheter 1 is pulled back into the sleeve 2, the assembly remaining attached to the tracheal tube connector so that it can be reused when necessary.

It has been found that the antimicrobial properties of the external surface 11 remain effective for a prolonged period despite being repeatedly displaced backwards and forwards through the sliding seal 50. The antimicrobial surface 11 minimizes the growth of bacteria on the catheter and enables the assembly to be used for periods of up to about 48 hours depending on how frequently the assembly is used. This is considerably longer than an equivalent assembly without any antimicrobial treatment which might typically be used for about 24 hours.

Alternative assemblies may include an antimicrobial substance on another component of the assembly that is effective to reduce transfer of bacteria from the catheter to the patient. For example, an antimicrobial substance on the inside of the sleeve 2 may help reduce microbial accumulation on the external surface of the catheter because of contact of the sleeve with the catheter during handling. Alternatively, an antimicrobial substance in the sliding seal 50 might help reduce transfer of bacteria from the catheter to the patient as the catheter is pushed through the seal.

What we claim is:

1. A method of removing undesirable fluid from the respiration passages of a patient by a suction catheter assembly including an aspirating catheter having a proximal end and a distal end, said distal end being suitable for insertion into a patient; a vacuum connecting member located in the vicinity of the proximal end of the aspirating catheter; a patient connecting member mounted to surround the aspirating catheter in the vicinity of the distal end of the aspirating catheter; a flexible protective sleeve extending along the aspirating catheter where it extends between the patient connecting member and the vacuum connecting member, the patient connecting member having a sliding seal with the external surface of the aspirating catheter, said method comprising the steps of:

(a) providing an antimicrobial substance of a solid material on at least one component of said suction catheter assembly that reduces transfer of bacteria from the external surface of the aspirating catheter to the patient, wherein the antimicrobial substance includes a silver compound with a binder selected from the group comprising alumino-silicate and hydroxyapatite;

(b) advancing the aspirating catheter through the patient connecting member into the trachea of the patient to effect suctioning of the respiration passages;

(c) withdrawing the aspirating catheter into the protective sleeve through the patient connecting member after suctioning such that the catheter is wiped by the sliding seal;

(d) maintaining the aspirating catheter within the protective sleeve except for the periods when the suctioning is being effected, with said antimicrobial substance at least substantially reducing accumulation of bacteria on said catheter when in the protective sleeve;

(e) repeating steps (b), (c), and (d) each time the suctioning of the respiration passages is indicated, wherein said antimicrobial substance of said solid material remains effective to reduce transfer of bacteria from the external surface of the aspirating catheter to the patient despite repeated movement of said aspirating catheter through said sliding seal, and whereby said substantially reduced accumulation of bacteria allows repeated, periodical insertion of said aspirating catheter into the patient's trachea.

2. A method according to claim 1, wherein an antimicrobial surface is provided by an antimicrobial substance incorporated into the material forming the catheter.

3. A method according to claim 1, wherein said external surface having antimicrobial properties is provided by coating the external surface of the catheter with a material having antimicrobial properties.

4. A method according to claim 1, wherein said substance having antimicrobial properties includes a silver compound.

5. A method according to claim 1, wherein the antimicrobial substance includes silver sulfadiazine.

6. A method according to claim 1, wherein the antimicrobial substance includes a silver compound with a polymer attachment substance.

7. A method according to claim 1, wherein the antimicrobial substance includes chlorhexidene.

8. A method according to claim 1, wherein the aspirating catheter is substantially of polyvinyl chloride.

* * * * *